US007940946B2

(12) United States Patent
Caldarola

(10) Patent No.: US 7,940,946 B2
(45) Date of Patent: May 10, 2011

(54) OPEN FIT CANAL HEARING DEVICE

(75) Inventor: James F. Caldarola, East Longmeadow, MA (US)

(73) Assignee: Anova Hearing Labs, Inc., Springfield, MA (US)

( * ) Notice: Subject to any disclaimer, the term of this patent is extended or adjusted under 35 U.S.C. 154(b) by 1123 days.

(21) Appl. No.: 11/604,154

(22) Filed: Nov. 27, 2006

(65) Prior Publication Data

US 2008/0123889 A1 May 29, 2008

(51) Int. Cl.
*H04R 25/00* (2006.01)
*H04R 25/02* (2006.01)
*A61B 7/02* (2006.01)

(52) U.S. Cl. ........ 381/328; 381/322; 381/324; 181/130; 181/135

(58) Field of Classification Search .................. 381/322, 381/324, 328; 181/135
See application file for complete search history.

(56) References Cited

U.S. PATENT DOCUMENTS

| | | | | | |
|---|---|---|---|---|---|
| 2,521,414 | A | * | 9/1950 | Schier | 181/135 |
| 4,006,796 | A | | 2/1977 | Coehorst | |
| 4,830,139 | A | | 5/1989 | Cirillo | |
| 4,869,339 | A | | 9/1989 | Barton | |
| 5,298,692 | A | | 3/1994 | Ikeda et al. | |
| 5,654,530 | A | * | 8/1997 | Sauer et al. | 181/130 |
| 5,920,636 | A | * | 7/1999 | Oliveira et al. | 381/328 |
| 6,009,183 | A | | 12/1999 | Taenzer et al. | |
| 6,097,823 | A | | 8/2000 | Kuo | |
| 6,324,291 | B1 | | 11/2001 | Weidner | |
| 6,339,648 | B1 | | 1/2002 | McIntosh et al. | |
| 6,810,987 | B1 | | 11/2004 | DeKalb | |
| 6,931,142 | B2 | | 8/2005 | Fushimi | |
| 7,027,608 | B2 | | 4/2006 | Fretz et al. | |
| 7,215,789 | B2 | * | 5/2007 | Shennib et al. | 381/328 |
| 2002/0085728 | A1 | | 7/2002 | Shennib et al. | |
| 2005/0123163 | A1 | | 6/2005 | Oliveira et al. | |
| 2005/0190940 | A1 | | 9/2005 | Ach-Kowalewski et al. | |
| 2005/0244026 | A1 | | 11/2005 | Nielsen et al. | |
| 2006/0067551 | A1 | | 3/2006 | Cartwright et al. | |
| 2006/0067556 | A1 | | 3/2006 | Bailey et al. | |

* cited by examiner

*Primary Examiner* — Curtis Kuntz
*Assistant Examiner* — Sunita Joshi
(74) *Attorney, Agent, or Firm* — Clark & Brody

(57) ABSTRACT

An improved hearing aid device adapted for use within the ear canal of the CIC (Completely In the ear) and of the partially exposed ITC (In The Canal) type. This aid consists of a system of integrated parts allowing an air gap to substantially surround the hearing aid shell and air passages which communicate with the inner ear minimizing occlusion sensations and providing the user with an enhanced natural hearing experience. A key aspect of this device is the provision of air passages in the mounting insert which securely positions the hearing aid shell in the wearer's canal. These passages are designed to stay open after insertion of the aid in the ear canal. In use, unamplified sound from the outside passes around the hearing aid shell, through the air passages in the mounting insert blending with the amplified sound emanating from the receiver. The area of air passages in the mounting insert can be tailored by the technician adapting to the hearing loss characteristics of the user. Surprisingly, acoustic feedback is mitigated in spite of the openness of this novel design.

27 Claims, 4 Drawing Sheets

OPEN FIT CANAL HEARING DEVICE

FIELD OF THE INVENTION

This invention relates to hearing aid devices in which the entire hearing aid including microphone, receiver, circuitry and power source are mounted substantially within the ear canal. This invention provides benefits to the ITE (In the ear), wherein the aid is partially exposed outside the ear canal, the CIC (Completely in the Canal) Aid and modifications between these types.

BACKGROUND OF THE INVENTION

A very thorough description of the Ear canal Anatomy is provided in published patent application Ser. No. 10/052,199 to Shennib et al the entirety of said specification is herein incorporated by reference.

Conventional hearing devices are typically characterized by the way they fit into the individual's ear and are:

1) Behind-The-Ear (BTE) type in which the main body consisting of the microphone, power source, amplifier and ear phone/receiver are mounted behind the ear and the sound tube communicating from the earphone to an ear mold which typically fits mostly in the concha or in some instances within the ear canal.
2) In-The-Ear (ITE) type fits largely in the auricle and concha cavity areas, extending minimally into the ear canal. (These are custom fitted)
3) In-The-canal (ITC) type which fits in the concha cavity and extends into the ear canal.
4) Completely-In-the-Canal (CIC) type which fits completely within the ear canal past the aperture.

Quite recently the "Open-fit" or "Over the Ear" OTE hearing aid have come to the market which are small BTE type hearing aids with a very small delivery sound tube connected to a soft silicone dome or highly vented acrylic tip that holds the tube within the ear canal. These open fit devices are designed to reduce the "occlusion effect", which is the amplification of your own voice when your ears are blocked. Occlusion effects are an annoying in that a users voice sounds unnaturally highter than normal since bone conduction becomes more pronounced as the ear canal is blocked. Teanzer et al. U.S. Pat. No. 6,009,183 and US Patent publication 2005/0190940 to Ach-Kowalewski et al, herein incorporated by reference depict earpieces that mount entirely within the ear canal. U.S. Pat. No. 7,027,608 to Fretz et al herein incorporated by Reference is illustrative of Open fit aids and discusses different ear tips which can be mounted to the sound tube of a BTE hearing aid. The tip of Fretz et al is normally open after insertion into a wearer's ear canal.

Nielsen et al, US patent publication 2005/0244026 describes a flexible earpiece for a hearing aid. The flexible earpiece is made of sidewalls which conforms to the wearer's ear canal and attaches to the base of the aid. While Nielsen illustrates that this earpiece connects with the sound tube of a BTE hearing aid, Nielsen do disclose that the earpiece can be used with the base from a hearing aid of the ITC type. The earpiece of Neilson is generally closed in use as the pressure applied to the sidewall by the wearer's ear canal will provide close contact between the overlapping parts of the sidewall so that no leaks occur along the edges of the sidewall. Neilsen et al can allow some air passage through an optional vent at the sidewall base.

US patent publication 2002/0085728 to Shennib et al is descriptive of and extend wear CIC hearing aid wherein the body of the aid is made smaller than a typical ear canal. This design is stated as being mass producible as these do not have to be custom fit to the wearer, as do conventional CIC aids. Shennib minimizes feedback by occluding the bony region with an insert preventing acoustic sound from entering the inner ear.

In general, occlusion in ITC, ITE and CIC aids is somewhat mitigated by a vent tube which provides communication between the ear canal behind the amplified sound source and the surroundings. However the presence of vent tubes or passageways between the amplified sound source and the surroundings leading to unwanted acoustical feedback, which must be carefully managed. Feedback is caused when amplified sound reenters microphone. Therefore, to limit feedback, most CIC devices the vent tube, designed to opening is limited to about 0.6 to 0.8 mm diameter.

U.S. Pat. No. 4,969,534 to Kolpe et al, herein incorporated by reference is illustrative of a typical ITC aid having a casing to which a hollow sleeve is attached which is compressed and inserted in the wears ear. The hollow sleeve allows only amplified sound from the receiver to be transmitted to the tympanic membrane.

SUMMARY OF THE INVENTION

The hearing device of the present invention pertains to devices which are inserted substantially within the ear canal and is an improvement over conventional ITE (in the ear), ITC (in the canal) and CIC completely in the canal aids in that it provides a natural sounding experience with a comfortable occlusion less fit in a design which mitigates acoustic feedback.

In the present invention a case, otherwise known as a shell, is made smaller than conventional CIC aids, which are custom formed to conform to the wearer's ear canal. Specifically, the case of the present invention has a generally elliptical cross section and is of a smaller cross section than that of an average wearer's ear canal when mounted in the wearer's ear. The case of the present invention is, by design, non-conformal to the wearer's ear canal so that a gap is provided around the case between the length of the case and the wearer's ear canal. This gap provides both a comfortable fit in that the case is in minimal contact with the wearer's ear canal. In addition, occlusion, or a blocked sensation experienced by the majority of CIC/ITC/ITE users is virtually eliminated. Also, the gap allows natural sounds from the surrounding to bypass microphone and blend with the sound emanating from the receiver section. As the case is designed of smaller cross section along the entire length of the case for most individuals, an impression for a conformal fitting is not necessary, making the hearing device of the present invention amenable to mass production.

Since the case of the present invention must be fixed within the ear canal to avoid unwanted movement of the hearing device, the case is affixed with a flexible mounting member attached to the tip portion of the receiver section, which is preferably an integral part of the casing.

The flexible mounting insert member of the present invention has openings to allow continued passage of natural sound from the gap formed upstream of the mounting insert to blend with amplified sound delivered from the receiver section. The flexible mounting member can take on a number of d resembling the "open fit" ear pieces conventionally used in "open fit" BTE aids. However, because of feedback issues particularly with wearer's having significant hearing losses at higher frequencies, there is a limit to how "open" the flexible mounting member can be.

The flexible mounting insert member has apertures made by perforating or slitting or cutting custom fabricating the insert member with openings. The mounting insert member can be prefabricated with openings at the factory or can be custom cut or the technician dispensing the aid can otherwise adjust the area manually. Alternatives include adjusting the open area of the flexible mounting by using pre-made mounts inserts having different opening areas or custom cutting or perforating or providing new or additional opening to a preformed insert member originally having no open area in the region between the mounting hub and the outer circumference of the insert.

One embodiment of the invention shows a feature wherein rotatable adjusting members comprising vane or blades and the like are rotated relative to the flexible mounting member already having an open area. The adjusting member effectively blocks off more or less area and is fixed once the wearer is satisfied with the adjustment. The adjusting member can also function to complement the mounting already provided by the mounting member. In many instances, such as a dome or propeller type ear piece the adjusting member can be a substantial duplicate of the flexible member. The position of the adjusting member relative to the mounting member can be retained by placing teeth on the mating surfaces of the adjusting and mounting members so to prevent relative movement once secured by a screw or other fastening means.

It is remarkable that providing an open case/open fit earpiece design does not produce a noticeable feedback when properly adjusted. Even without the use of active feedback control, it has been discovered that proper selection or adjustment the mounting member with the appropriate open area eliminates unwanted feedback. As the inventive design does not require a vent tube one explanation is that feedback is mitigated by the return of amplified sound to the periphery of the case which is more distant from the microphone than from the conventional hearing aids with vent tubes. It also may be that higher frequency sounds emanated by the receiver are redirected and absorbed at least in part by the mounting member and also by the ear canal itself in the opportunistic gap intentionally provided by the smaller case design of the present invention relative to the canal. Further dampening of the returned amplified sound can be achieved by the use of flexible elastomeric materials as known in the art such as silicone surrounding at least in part, the case.

Once fitted with prototype hearing aids of the present invention, with either the propeller type or perforated dome type both without active feedback control, long time hearing aid wearer's, including some candidate veteran BTE customers, were exuberant over the comfort and natural hearing experience provided with these aids.

There is logically an upper limit as to the hearing losses that can be accommodated with this aid and are comparable with conventional CIC aids.

DESCRIPTION OF THE PREFERRED EMBODIMENTS

Figure 1:
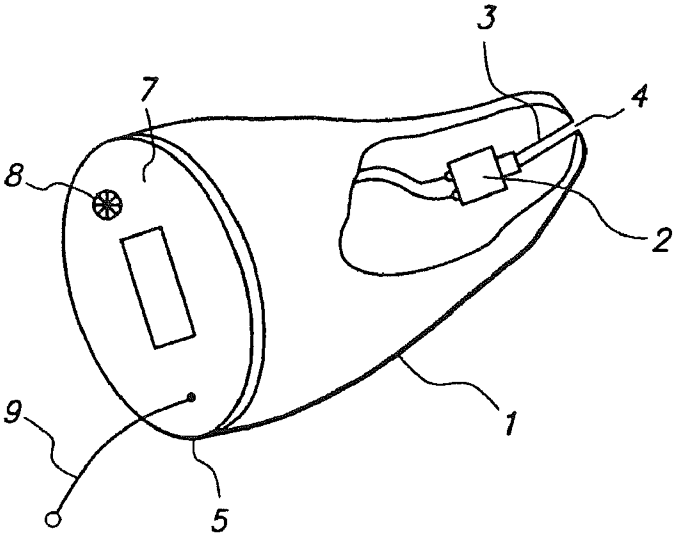
FIG. 1 (Prior Art)
FIG. 1 shows a cutaway view of a CIC type conventional Hearing aid

FIG. 1 shows the prior art CIC type hearing aid device. The case or shell 1 is shaped for insertion and conforming to the wearer's ear canal. The case 1 houses a microphone element (not shown), battery source, amplifier circuitry that amplifies the electric voltage generated by the microphone element. The amplified voltage signal is passed to a receiver element converting the amplified voltage signal to an acoustical wave which is directed through the receiver tube 3 leading to receiver opening 4. Receiver opening 4 is directed towards the wearer's inner ear.

Faceplate 5 is mated to the case 1 providing the wearer access to the battery compartment by way of battery door 6. Microphone opening 7 is positioned on faceplate 1, which directs incoming surrounding sound into the microphone element (not shown). Optional on/off volume control 8 are often provided as well as aid removal means 9, which can be any protrusion to assist the wearer to remove the device for cleaning, battery replacement or adjustment.

Figure 2:
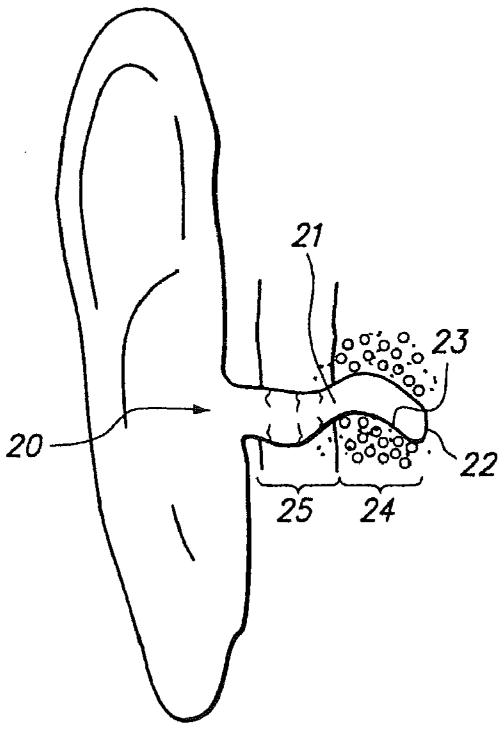
FIG. 2 (Prior Art)
FIG. 2 Depicts a the general anatomy of the human ear pertaining to the fitment of CIC/ITC hearing aid device

FIG. 2 shows the overall anatomy of the ear as it relates to the placement of CIC/ITC hearing devices. Canal aperture 20 or opening leads to the ear canal 21 which is about 25 mm and leads to the eardrum 22. Bend area 23, which is typically referred to as the first bend is characteristic of most individuals and separates the bony region 24, from the cartilaginous region 25. The cartilaginous is relatively soft in comparison with the bony region 24. Most CIC devices are custom molded to conform substantially to cartilaginous region 25.

Figure 3:
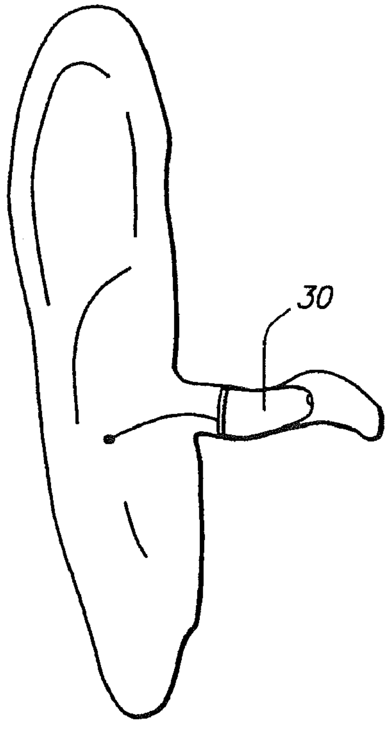
FIG. 3 (Prior Art)
FIG. 3 shows a conventionally mounted CIC hearing aid device in a fitted position within the ear canal

FIG. 3 depicts a conventionally mounted CIC hearing aid device 30 in a fitted position within the ear canal. Note that this aid conforms to the ear canal forming an effective seal and reducing the conventional problems of direct acoustic feedback.

Figure 4:
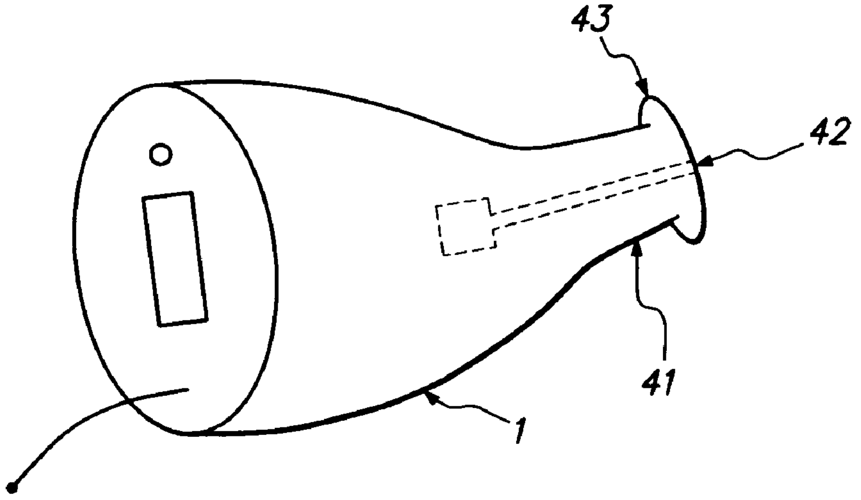
FIG. 4 shows the aid of the present without the mounting insert.
Figure 5:
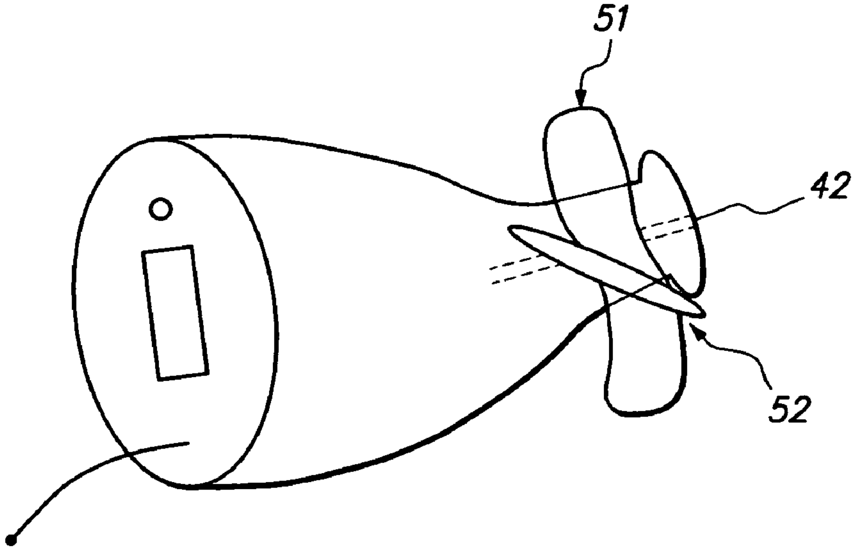
FIG. 5 illustrates the aid of the present invention with the perforated mounting insert.

FIGS. 4 and 5 shows the CIC type aid of the present invention which consists of a case 1 which narrows towards a protrusion housing with sound tube opening 42 at the protrusion tip. The case is smaller than conventional CIC aids in that when positioned in the wearer's ear canal for use, an air gap is formed substantially around the case 1. At the end of the protrusion 41 is a retaining nub 43, which affixes the flexible mounting insert 51 of FIG. 5 to the case 1. It is to be also noted that when mounting insert 51 is mounted in the bony region of the wearer ear canal, an open area is still present in the installed insert 51. These openings allow passage of surrounding acoustic waves which enter through aperture 1 of FIG. 1 and around case 1 of FIG. 4 to blend with the amplified sound exiting the sound tube opening 3 of FIG. 1 and be directed towards the ear drum 22 of FIG. 2.

Figure 6:
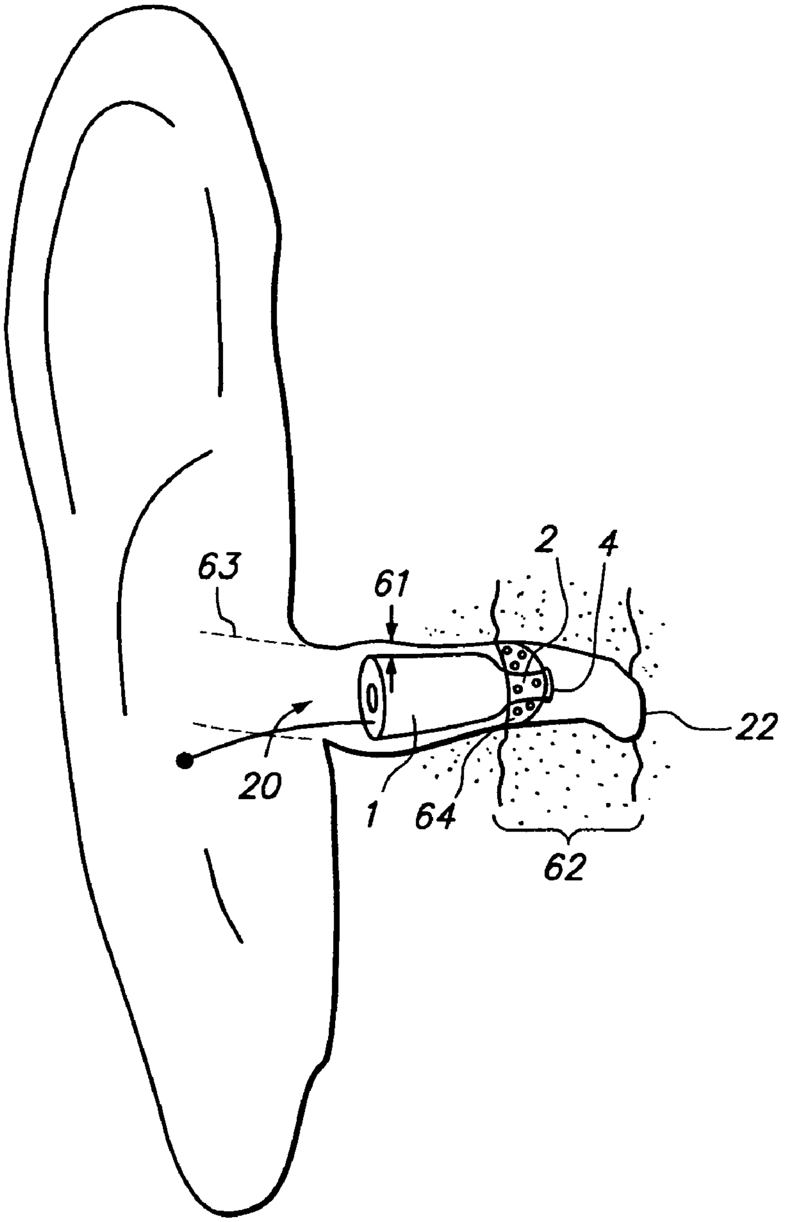
FIG. 6 Illustrates the aid of the present invention with the perforated mounting insert in a normally mounted position within the wearer's ear.

FIG. 6 depicts the CIC type aid of the present invention after being mounted in a wearer's ear canal. It is readily apparent that case 1 is smaller in cross section than the wearer's ear canal along its entire length. The average minimum gap 61 between the case at any point along its length and the wearer's ear canal is about 0.1 nm. Again, this gap is formed substantially between the entire surface of the case and the wearer's ear canal and reduces the occlusion effect, providing the wearer with the perception of natural sounding experience. Maximum average gap distances between the wearer's ear canal and the case ranges from about 2 to about 4 mm. Larger gap sizes tend to cause unwanted feedback even for modest acoustical gains. The cross sectional area of case 1 is generally elliptical and narrows along its length to the point at which the protrusion is formed on the case. Again at the end of the protrusion 2 is a nub 4, which retains the mounting insert 64. FIG. 6 depicts the use of a perforated dome mounting insert, although a propeller type mounting insert 51 can also be used as depicted in FIG. 5. Alternatively, there are a number of alternative mounting members that can be affixed to the case tip 2 of FIG. 6 using a variety of mounting means and is shown if FIGS. 7 A-E.

FIG. 6 also depicts that the mounting insert comes in substantial contact with the bony region 62 of the ear canal generally beyond the first bend. This serves to stabilize the non-conformal case inside the wearer's ear canal. Additional stabilizing means which do not substantially interfere with the acoustical pathway provided between the inner ear, through the mounting insert and along the length of the case can be affixed to the case as required. This can be for example flexible mounting ribs which are affixed along the length of the case (not illustrated).

As explained earlier, openings are advantageously added to the mounting insert, these openings allow passage of surrounding acoustic waves 63, which enter through aperture 20 and around case 1 to blend with the amplified sound exiting the sound tube opening 3 and be directed towards the eardrum 22 of FIG. 6.

Figure 7A:
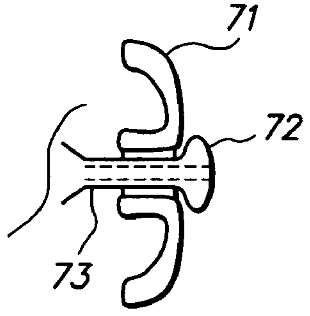
FIGS. 7 A and FIG. 7B show different views of an domed insert with openings formed or cut into it.
FIG. 7C illustrates the use of a washer abutting the domed insert to provide variable open area of a fixed perforated area dome insert.
FIGS. 7D and 7E shows different views of a perforated concave insert which open area is adjusted by means of another perforated concave insert which rotatably abuts the other insert allowing the effective open area of the combined insert to be adjusted.
Figure 7B:
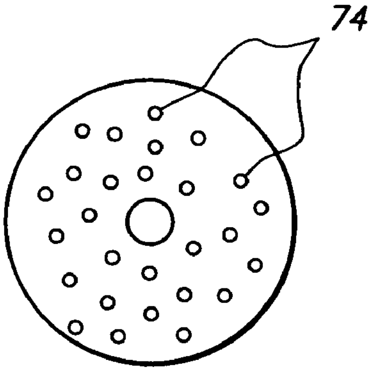

FIGS. 7A and 7B, for example, shows a domed type insert 71 mounted and retained by nub 72 at the end of protrusion 73. The dome is provided with slits or openings, which can be preformed at the factory or custom cut by the technician fitting the aid. For users with more pronounced high frequency losses, less open areas is provided in the mounting insert by employing by decreasing the number and/or area of the openings. The openings can be of any shape including slits, perforations, apertures and the like and are formed in the shaped mounting insert either before or after manufacture. It is important that in the blade or vaned type mounting inserts, the projecting vanes or blades, which emanate substantially radially from the hub portion do not touch to the extent that openings are closed after operational placement of the case into the wearer's ear canal.

FIG. 7-C shows insertion of a washer element 75 inside the closed portion of the domed insert 71 serving to restrict air passages 74. The domed insert may be prefabricated at the factory. This allows the fitter to tailor the degree of occlusion by swapping out washer elements of varying outside diameters to effectively block more or less of air passages 74. This design permits manufacture of just a few standardized dome inserts with pre-made openings for adjustment with customized off-the-shelf washers to accommodate users with varying hearing losses and canal shapes to optimally reduce the wearer's occlusion effect. Though not illustrated, washers can also be used in tandem with the propeller type insert 51 (FIG. 5) or in conjunction with other inserts with fixed apertures.

Figure 7C:
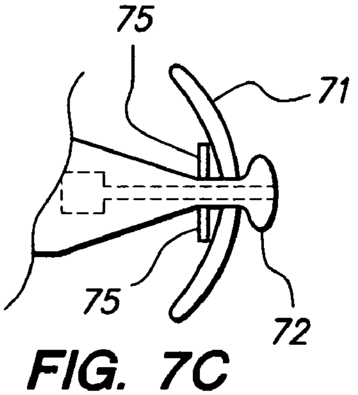
Figure 7D:
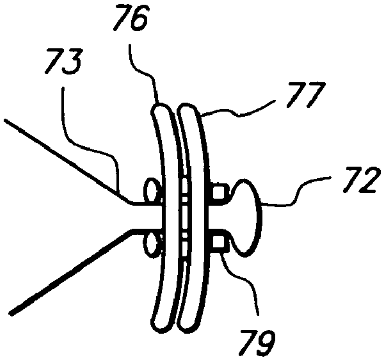
Figure 7E:
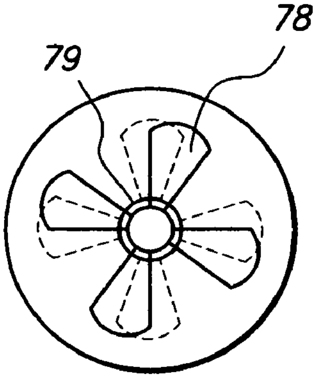

FIGS. 7D and 7E show a "salt-shaker" design wherein two domed inserts 76 and 77 with open areas 78 abut each other while mounted on protrusion 73 in tandem. Rotation of insert 76 relative to insert 77 provides adjustable opening areas 78. Gripping ring 79 also militates against accidental rotation of the inserts after adjustment. During adjustment, the fitter simply rotates one insert against the other to vary the occlusion effect to consistent with the specific hearing loss and geometry of the wearer's ear canal.

EXAMPLE 1

A wearer with moderate hearing loss was fitted with a custom molded conventional digital type CIC hearing aid, without active feedback control and conforming to the wearer's ear canal. The aid was vented by means of a 0.8 mm vent tube extending near the case tip and through an opening in the faceplate. The aid was then completely inserted into the wearer's ear and retained through contact with the wearer's ear canal. The aid is adjusted to provide sufficient amplification to the satisfaction of the wearer.

EXAMPLE 2

The same hearing aid circuit of Example 1 was placed in a smaller diameter case, but without the conventional vent tube arrangement described in Example 1. The case tip was then fitted with the propeller type insert 51 of FIG. 5. The open area of the propeller insert was about 50% in its unmounted state. The insert 51, was then secured in the wearer's inner ear by contact of the flexible propeller insert substantially within the bony region of the wearer's ear canal. An average air gap of about 1 mm was formed around the case and along its length. As the case is substantially concentrically mounted within the ear canal, a substantially annular gap is formed between the case and the ear canal. The propeller insert provided about 40% open area after being mounted. The wearer commented immediately on the comfort of the fit and also commented that he could hear more naturally not hearing his own voice when he talked. This aid provided 25% db of gain, without feedback.

EXAMPLE 3

The same hearing aid circuit and case of Example 2 was then compared using a domed insert mounted at the case tip end. The domed insert was fitted with openings around near central portion of the dome so that they would not be blocked after insertion into the wearer's ear. The open area was estimated at 25% after insertion of the aid into the wearer's ear. This aid provided a 30% improvement of gain with similar favorable responses in Example 2.

EXAMPLE 4

The same hearing aid of Example 3 was fitted with a closed dome insert with no openings in the dome. Although a 37 db gain was possible, the same wearer although experiencing the same comfort levels of Examples 2 and 3, did experience echoing and complained about hearing his own voice in comparison with the other aids tested in Examples 1, 2 and 3.

In summary, Example 4 illustrates the use of a non apertured insert in a non-conformal shell arrangement (ie case is not molded in conformance with the wearer's ear canal) providing minimal contact with the wearer's ear canal. While this example is an improvement over example 1 in terms of comfort, Examples 2 and 3, having passageways in the insert which are not blocked when fully inserted in its normal operating position, additionally decreases the occlusion effect, providing a more natural hearing experience.

When fitting a wearer with moderate hearing loss, the use of an open propeller type insert having about a 10-60% open area and more preferably 25-50% open area after mounting has been found to provide adequate gain while significantly reducing complaints involving occlusion.

Apertured dome inserts in general, provide less open area than propeller type inserts as there is a limit to the amount of apertures which can be made in the dome insert before structural integrity of the insert is compromised. Apertured dome of the present invention would have a maximum open area of about 45% in its mounted position, before the dome starts to lose its structural integrity. Improvements such as the use of variable wall thickness, with more thickness in the central portion of the dome can serve to improve the structural integrity at higher open areas. In any event, apertures or perforation are usually made towards the center of the domed insert as it would otherwise be blocked when mounted in its normal operating position.

To achieve gains in excess of about 30 db gain it is preferable to use the apertured dome type instead of the propeller type, as the dome type can provide further restriction of air compared to the more open "propeller" type insert. Typical open areas before and after mounting are about 30 and 25% respectively.

For gains in excess of about 30 db, even smaller open areas are required to minimize feedback which then decreases in the feeling of openness experienced by the wearer.

In practice, adjustment of the open area of the insert can be accomplished in one piece insert by selectively puncturing the insert to open it up before the point in which feedback is noticed by the user. The disadvantage if this method is that the process must be repeated on a new insert if too much openness is provided before the wearer notices feedback sounds. Even with a minimal opening of 5% near in the central portion of the otherwise closed dome insert was enough to provide the wearer's with significant hearing loss increased relief from the occlusion effect.

Alternatively, a series of pre-formed domes of with open areas ranging from 5% to about 60% can be utilized so that at the onset of feedback, the domed inserted is swapped out with another insert of less open area. It should be also kept in mind that each pre-formed dome be sized to comfortably fit when mounted substantially in the wearer's inner ear. As the diameter of the wearer's ear canal varies from person to person, a series of pre-formed inserts of varying diameters is preferably utilized. The hole or opening pattern is made in the area generally between the hub area of the "dome" or equivalent insert to the outer periphery of the dome that will not come into contact with the inner ear. Any hole or opening pattern can be used, both symmetrically and non-symmetrically placed in the insert. Also, different sizes and shapes of openings can be employed in combination within a specific hole pattern on the domed or equivalent insert.

Alternatively, the variable apertured design of the inventive "washer" type of FIGS. 7A, 7B or the salt shaker design of FIGS. 7C, and 7D are advantageous in that they can be adjusted to minimize occlusion complaints and then backed off to decrease open area when feedback becomes noticeable.

In addition, the use of active feedback control as is well known in the art is advantageously incorporated into the circuitry of the aid to further militate against unwanted feedback sounds. U.S. Pat. No. 6,097,823 to Kuo, herein incorporated by reference, is illustrative of the use of active feedback control in a hearing aid circuit to minimize unwanted feedback allowing the fitter to provide a more open insert for any given hearing loss. The incorporation of active feedback control is more advantageous when fitting wearer's with significant hearing losses in that it does allow the use of a more open insert compared to when active feedback control is not utilized.

In summary, the advantages of the present invention over the prior art should be quite apparent as it provides wearer's with relief from occlusive sounds while providing a comfortable fit compared with conventional CIC aids. As a gap between the case and the wearer's ear canal is permissible in this particular CIC device, the use of a non-custom molded or in other words a "prefabricated" case is advantageously employed. This allows the wearer to be fitted with a prefabricated case of standard size and shape unlike conventional CIC requiring custom molding from an impression made for the specific wearer.

Modifications to the present invention include all enhancements conventionally applied to ITC type hearing aids including the use of wax filters inserted in the receiver section of the aid, rechargeable batteries, alterations of the materials of construction of the case and mounting insert, geometry of the insert etc.

The invention claimed is:

1. A hearing device adapted for insertion substantially within the ear canal, said device comprising:

a case having a power source, a microphone, a receiver element, and an acoustic passageway, wherein said case, when mounted in the ear canal, provides at least one open passageway formed along the case and between the ear canal and the case;

a flexible insert attached to the case, the flexible insert provided with at least one opening to create a sound path extending through the at least one open passageway and the at least one opening, wherein the flexible insert further comprises at least one generally concave element or at least one bladed element, wherein the at least one bladed element forms openings which have a total open area of about 5% to about 70% when the at least one bladed element is in a mounted position.

2. The device of claim 1 wherein the size of the case anywhere along its length is on average at least 0.1 mm smaller than the size of the wearer's ear canal when fitted.

3. The device of claim 1 wherein the flexible insert is the at least one generally concave element, which has a plurality of openings.

4. The device of claim 3 wherein said openings form a total open area from about 0.5% to about 35% in said flexible insert.

5. The device of claim 3 wherein said openings form a total open area from about 5% to about 25% in said flexible insert.

6. The device of claim 3 wherein said openings form a total open area from about 5% to about 20% in said flexible insert.

7. The device of claim 3 wherein a thickness of the generally concave element increases towards the center.

8. The device of claim 3 wherein said at least one generally concave element is rotatably mounted against another concave apertured element to allow adjustment of said open area.

9. The device of claim 3 wherein a disc element is positioned in tandem with said at least one generally concave element to allow adjustment of open area in said mounting insert.

10. The device of claim 1 wherein said flexible insert is the at least one bladed element, which has flexible blades extending substantially in a radial direction from a hub.

11. The device of claim 10 wherein the total open area is from about 25% to about 60%.

12. The device of claim 10 wherein the total open area is from about 30% to about 50%.

13. The device of claim 10, wherein said flexible blades are curved.

14. The device of claim 1 wherein an area of the at least one opening is adjustable.

15. The device of claim 10 wherein at least one disc element is positioned in tandem with said at least one bladed element allowing adjustment of the total open area.

16. The device of claim 1 wherein said flexible insert is provided at least one perforation of at least 0.75 mm in diameter.

17. The device of claim 1 wherein said flexible insert is the at least one generally concave element, which has a total open area in from about 5% to about 70%.

18. The device of claim 17 wherein the total open area from about 15% to about 50%.

19. The device of claim 17 wherein the total open area from about 2% to about 25%.

20. The device of claim 1 wherein additional mounting means are affixed to said case to support said hearing device within the ear canal.

21. The device of claim 20 wherein said additional mounting means comprises flexible ribs attached to the outside of the case extending along the outside of said case.

22. The device of claim 1 further comprising active feedback reduction in the amplification circuitry.

23. The device of claim 1 wherein said case is prefabricated to a standard size and shape thereby avoiding custom molding to the wearer's ear canal.

24. The device of claim 1, wherein a plurality of open passages are provided by the case.

25. The device of claim 1, wherein the case does not have a vent tube.

26. The device of claim 1, wherein the fitted cross sectional dimension of the case is on average from about 0.5 mm to about 2 mm less than that of a user's ear canal at any cross section of said case.

27. The device of claim 1, wherein the fitted cross sectional dimension of the case is on average from about 0.5 mm to about 6 mm less than that of a user's ear canal at any cross section of said case.

* * * * *